US007045322B1

(12) United States Patent
Kurita et al.

(10) Patent No.: US 7,045,322 B1
(45) Date of Patent: May 16, 2006

(54) PROCESS FOR PRODUCING LYSOSPHINGOLIPIDS

(75) Inventors: Toyohisa Kurita, Otsu (JP); Hiroyuki Izu, Kusatsu (JP); Mutsumi Sano, Otsu (JP); Ikunoshin Kato, Uji (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/647,135

(22) PCT Filed: Mar. 30, 1999

(86) PCT No.: PCT/JP99/01610

§ 371 (c)(1),
(2), (4) Date: Sep. 27, 2000

(87) PCT Pub. No.: WO99/50433

PCT Pub. Date: Oct. 7, 1999

(30) Foreign Application Priority Data

Mar. 31, 1998 (JP) .................................. 10-101745

(51) Int. Cl.
*C12N 9/00* (2006.01)
(52) U.S. Cl. ..................................................... 435/183
(58) Field of Classification Search .................. 435/84, 435/183
See application file for complete search history.

(56) References Cited

U.S. PATENT DOCUMENTS

| 3,926,726 A | * | 12/1975 | Antonini et al. ............... 435/52 |
| 4,997,760 A | | 3/1991 | Hirabayashi et al. ........ 435/227 |
| 5,108,916 A | * | 4/1992 | Cobbs et al. ................. 435/135 |
| 5,143,841 A | | 9/1992 | Hirabayashi et al. ........ 435/227 |
| 5,350,871 A | | 9/1994 | Geluk et al. |
| 5,610,040 A | | 3/1997 | Smeets et al. |
| 5,700,668 A | | 12/1997 | De Ferra et al. |

FOREIGN PATENT DOCUMENTS

| EP | 0 707 063 | 4/1996 |
| EP | 0940409 A | 9/1999 |
| JP | 64 60379 | 3/1989 |
| JP | 5-317065 A | 12/1993 |
| JP | 6 78782 | 3/1994 |
| JP | 7 107988 | 4/1995 |
| JP | 8 845875 | 4/1996 |
| JP | 10 14563 | 1/1998 |
| JP | 9-173092 A | 1/2005 |

OTHER PUBLICATIONS

Brink et al., Enzyme Microb. Technol., 1988, vol. 10, pp. 736-743.*
Hirabayashi et al., "A Novel Glycosphingolipid Hydrolyzing Enzyme, Glycosphingolipid Ceramide Deacylase, Which Cleaves the Linkage between the Fatty Acid and Sphingosine Base in Glycosphingolipids", *J. Biochem* (1988), vol. 103, pp. 1-4.
Ito et al, "A Novel Enzyme That Cleaves the N-Acyl Linkage of Ceramides in Various Glycosphingolipids as Well as Sphingomyelin to Produce Their Lyso Forms", *The Journal of Biological Chemistry*, (1995), vol. 270, No. 41, pp. 24370-24374, The American Society for Biochemistry and Molecular Biology, USA.
Ashida et al., "Formation of Lyso-glycosphingolipids by *Sterptomyces* sp.", *Biosci, Biotech. Biochem.*, (1995), vol. 59, No. 11, pp. 2028-2032.
Barnholz et al., "Enzymatic Hydrolysis of Sphingolipids", *The Journal of Biological Chemistry*, (1966), vol. 241, No. 16, pp. 3731-3737, USA.
Yavin et al., "Enzymatic Hydrolysis of Sphingolipids. VIII. Further Purification and Properties of Rat Brain Ceramidase", *BIOCHEMISTRY*, (1969) vol. 8, No. 4, pp. 1692-1698.
Nilsson, "The Presence of Sphingomyelin- and Ceramide-Cleaving Enzymes in the Small Intestinal Tract", *Biochim. Biophys. Acta*, (1969), vol. 176, pp. 339-347.
Ito, M., "Sphingolipid Engineering Using Two Novel Enzymes", Bioscience To Industry, (1997) pp. 321-325, vol. 55 No. 5.

* cited by examiner

*Primary Examiner*—Michael Meller
(74) *Attorney, Agent, or Firm*—Browdy and Neimark, PLLC

(57) ABSTRACT

A process for producing lysosphingolipids by using an enzyme capable of specifically hydrolyzing the acid amide bond between a sphingoid and a fatty acid in a sphingolipid, characterized in that the enzyme reaction is carried out in a two-phase system liquid reaction mixture containing at least an organic solvent forming an aqueous phase and a separation phase in the presence of, if desired, a surfactant.

3 Claims, 5 Drawing Sheets

PROCESS FOR PRODUCING LYSOSPHINGOLIPIDS

CROSS REFERENCE TO RELATED APPLICATION

The present application is the national stage under 35 U.S.C. 371 of PCT/JP99/01610, filed 30 Mar. 1999.

TECHNICAL FIELD

The present invention relates to a process for producing a lysosphingolipid. More specifically, the present invention relates to an industrially useful process for producing a lysosphingolipid which is useful for cosmetics, pharmaceuticals, sphingo technology, cell technology and the like as well as a lysosphingolipid obtained by said process for production.

BACKGROUND ART

Lipids that have a sphingoid backbone as a common structure such as a sphingoglycolipid, a sphingophospholipid (including a sphingophosphonolipid) and a ceramide are collectively designated as sphingolipids. The amino group of the sphingoid backbone binds a long chain fatty acid having heterogeneous chain length through an acid amide bond to form a ceramide.

Recently, it has proved that the sphingolipid is widely distributed in organisms including lower animals and higher animals and plays important roles in biological activities such as growth, induction of differentiation and apoptosis in cells. In addition, the sphingolipid, which is a component of cellular membrane, has been used as an additive for cosmetics or pharmaceuticals.

An N-deacylated form (lyso-form) of the sphingolipid that lacks the fatty acid, which is attached to the amino group of the sphingoid in the sphingolipid through the acid amide bond, is designated as a lysosphingolipid. It has proved that the lysosphingolipid has similar and different biological activities as compared with those of the sphingolipid.

Since the lysosphingolipid has a free amino group in the sphingoid, it is useful as a starting material for synthesizing a lysosphingolipid derivative (a sphingolipid derivative or a sphingolipid analogue) by re-acylation. For example, a sphingolipid having a homogeneous fatty acid composition, a sphingolipid having different fatty acid chain length from that of the starting sphingolipid, or a novel sphingolipid containing a functional fatty acid such as docosahexaenoic acid can be synthesized. Alternatively, a sphingolipid labeled with a chromophore, a radioisotope or the like can be obtained. Furthermore, immobilization to a carrier can be achieved by utilizing the free amino group of the lysosphingolipid.

Conventional processes for producing a lysosphingolipid include a chemical process, a process in which an enzyme is used and a process in which a microorganism is used.

A hydrazinolysis method and a method of alkaline hydrolysis in an alcoholic solvent are known for chemically obtaining a lysosphingolipid from a sphingoglycolipid. However, when a glycosphingolipid that contains a sialic acid (a ganglioside) is used, for example, deacylation reaction of the sialic acid portion proceeds simultaneously in such methods. Furthermore, the N-acetyl group is eliminated when a sphingoglycolipid that contains an amino sugar is used, resulting in a de-N-acetyl lysoglycolipid. A very complicated procedure is required to make the deacylated lysoglycosphingolipid to have a sugar chain identical with a naturally occurring one. In one exemplary procedure, a protective group is selectively introduced to the amino group of the lipid portion, the sialic acid portion is re-acylated, and the protective group is then detached. In another exemplary procedure, the sugar portion is selectively re-acylated after incorporation into liposome. Furthermore, various by-products are generated in these procedures. As described above, a great deal of labor and a technical skill are required for producing a lysosphingolipid by a chemical process.

A process using hydrochloric acid-hydrolysis in an alcoholic solvent is generally used for chemically obtaining a lyso-form of one of sphingophospholipids, a sphingomyelin. However, various by-products are generated by using such a process. For example, a steroisomer with a sphingoid of L-threo-type (2S, 3S) is formed in addition to a naturally occurring one of D-erythro-type (2S, 3R). Consequently, the yield of the naturally occurring D-erythro-form of interest is low, and it is very difficult to purify the D-erythro-form from the reaction mixture.

On the other hand, processes in which an enzyme that generates a lyso-form from a sphingolipid is used are known to date. The following processes are known: a process in which ganglioside ceramidase produced by an actinomycete of genus Nocardia is used [Journal of Biochemistry, 103:1–4 (1988); JP-A 64-60379]; a process in which an enzyme produced by an actinomycete of genus Rhodococcus or a processed product of the cells is used [JP-A 6-78782]; a process in which sphingolipid ceramide N-deacylase produced by a bacterium of genus Pseudomonas is used [Journal of Biological Chemistry, 270:24370–24374 (1995); JP-A 8-84587]; a process in which sphingolipid ceramide N-deacylase produced by a non-fermentative Gram-negative bacillus AI-2 is used [JP-A 10-257884]; and a process in which ceramidase produced by a bacterium of genus Pseudomonas s used [JP-A 10-14563].

However, the reaction yield of a lyso-form in the processes using these enzymes is not satisfactory. For example, when sphingolipid ceramide N-deacylase is used, although the yield varies depending on the substrate used, the yield from ganglioside GM2 (which is the most susceptible substrate to hydrolysis) is at most approximately 70%, whereas that from ganglioside GM1 is at most approximately 60%.

Processes for producing a lysosphingolipid in which the following microorganisms or extracts therefrom are used are known: an actinomycete of genus Streptomyces capable of producing glycosphingolipid ceramide deacylase [Bioscience, Biotechnology, and Biochemistry, 59:2028–2032 (1995); JP-A 7-107988]; and a bacterium of genus Pseudomonas or genus Shewanella which produces sphingolipid ceramide N-deacylase [JP-A 10-45792].

However, a reaction contains a large amount of impurities such as a dye, a glycolipid or the like derived from a culture medium or cells in addition to a lyso-form of interest in a process in which a substrate is added to the medium. Therefore, a complicated purification procedure has been required to obtain the lyso-form with high purity in such a process. Furthermore, it has been very difficult to handle a small amount of the sphingolipid to purify the lyso-form in the process for the reasons as described above.

In all of the conventional processes for producing a lysosphingolipid by using an enzyme, or a microorganism or an extract therefrom, the reaction is conducted only in an aqueous system. No process using a two-phase system consisting of an aqueous phase and a phase of an organic solvent that forms a separation phase immiscible with the aqueous phase has been known.

OBJECTS OF INVENTION

As described above, the conventional processes in which a lysosphingolipid is produced chemically, enzymatically or by the use of a microorganism were inefficient, generating undesirable by-products, resulting in a low reaction yield, and requiring a great deal of labor and technical skill for purification.

Accordingly, one object of the present invention is to provide a process for efficiently producing a lysosphingolipid without generating by-products.

Another object of the present invention is to provide a lysosphingolipid obtained by the above-mentioned process.

These and other objects and advantages of the present invention will be apparent from the description below with reference to the attached drawings.

SUMMARY OF INVENTION

Figure 1:
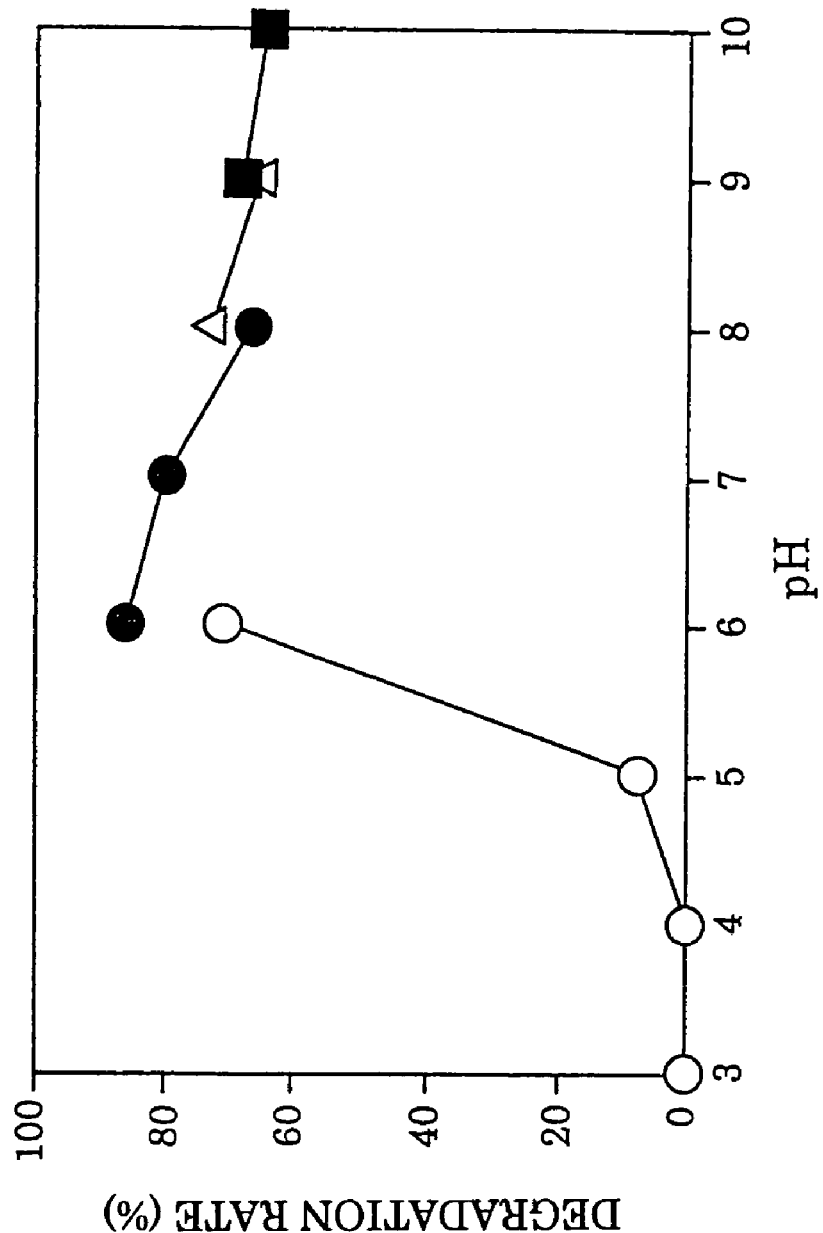
FIG. 1 depicts the optimal pH for the yield of a lyso-form in the presence of an organic solvent.

The present inventors have examined an industrially advantageous process for preparing a large amount of lysosphingolipid with high purity, and found that a lysosphingolipid can be produced without generating by-products, with an excellent reaction yield and with high purity. This can be achieved by conducting an enzymatic reaction in a two-phase system reaction mixture containing an organic solvent that is immiscible with water for producing a lysosphingolipid using an enzyme that specifically hydrolyzes an acid amide bond between a sphingoid and a fatty acid in a sphingolipid. Furthermore, the present inventors have intensively examined the organic solvent that is immiscible with water to be used and surprisingly found that the yield of the lysosphingolipid greatly varies depending on the fat-soluble organic solvent used. In addition, the present inventors have found that a lysosphingolipid can be produced more efficiently by adding one or more surfactant to the two-phase system reaction mixture. Thus, the present invention has been completed.

Thus, the present invention provides the following:

1. A process for producing a lysosphingolipid by using an enzyme that specifically hydrolyzes an acid amide bond between a sphingoid and a fatty acid in a sphingolipid, wherein an enzymatic reaction is carried out in a two-phase system reaction mixture containing at least one organic solvent which is immiscible with water;
2. The process for producing a lysosphingolipid according to (1) above, wherein the enzymatic reaction is carried out in the presence of at least one surfactant;
3. The process for producing a lysosphingolipid according to (1) or (2) above, wherein the organic solvent is selected from the group consisting of a hydrocarbon, an alcohol, an ester and an ether;
4. The process for producing a lysosphingolipid according to (3) above, wherein the hydrocarbon is an hydrocarbon of six carbons or more;
5. The process for producing a lysosphingolipid according to (3) above, wherein the alcohol is an alcohol of eight carbons or more;
6. The process for producing a lysosphingolipid according to (3) above, wherein the ester is composed of a carboxylic acid of six carbons or more and an alcohol of two carbons or more;
7. The process for producing a lysosphingolipid according to (3) above, wherein the ether is selected from the group consisting of phenyl ether, ethylene glycol diethyl ether, diisopropyl ether and vinyl ethyl ether;
8. The process for producing a lysosphingolipid according to (2) above, wherein the surfactant is selected from the group consisting of a surfactant having a steroid backbone, polyoxyethylene alkyl phenyl ether, polyoxyethylene sorbitan alkyl ether and polyoxyethylene alkyl ether; and
9. A lysosphingolipid obtained by the process according to any one of (1) to (8) above.

As used herein, "™" means a trademark.

DETAILED DESCRIPTION OF THE INVENTION

Sphingolipids used as a substrate in the present invention include a naturally occurring or synthetic substance having a long chain base, a sphingoid, including a sphingoglycolipid, a sphingophospholipid and a ceramide, alone or a mixture thereof.

A lysosphingolipid means an N-deacylated form of a sphingolipid lacking a fatty acid attached to the amino group of a sphingoid through an acid amide bond herein.

There is no limitation regarding an enzyme used in the present invention that specifically hydrolyzes an acid amide bond between a sphingoid and a fatty acid in a sphingolipid. The enzymes may be a known enzyme that releases an fatty acid from a sphingolipid, and include, for example, the following: ganglioside ceramidase produced by an actinomycete of genus *Nocardia* [Journal of Biochemistry, 103: 1–4 (1988); JP-A 64-60379]; an enzyme produced by an actinomycete of genus *Rhodococcus* [JP-A 6-78782]; glycosphingolipid ceramide deacylase produced by an actinomycete of genus *Streptomyces* [Bioscience, Biotechnology, and Biochemistry, 59:2028–2032 (1995); JP-A 7-107988]; sphingolipid ceramide N-deacylase produced by a bacterium of genus *Pseudomonas* [Journal of Biological Chemistry, 270:24370–24374 (1995); JP-A 8-84587]; sphingolipid ceramide N-deacylase produced by a bacterium of genus *Shewanella* [JP-A 10-45792]; ceramidase produced by a bacterium of genus *Pseudomonas* [JP-A 10-14563]; ceramidase derived from a mammalian tissue [Journal of Biological Chemistry, 241:3731–3737 (1966); Biochemistry, 8:1692–1698; Biochimica et Biophysica Acta, 176:339–347 (1969); Science, 178:1100–1102 (1972)]; an invertebrate ceramidase [WO 98/03529].

Among these, the sphingolipid ceramide N-deacylase produced by a bacterium of genus *Pseudomonas* and the sphingolipid ceramide N-deacylase produced by a bacterium of genus *Shewanella* have wide substrate specificity and are particularly preferable for the production of various lysosphingolipids.

The bacterial strain of genus *Pseudomonas* that produces sphingolipid ceramide N-deacylase, *Pseudomonas* sp. TK-4, is identified as G-182 and has been deposited on Jun. 24, 1994 (date of the original deposit) under Budapest Treaty under accession number FERM BP-5096. The bacterial strain of genus *Shewanella* that produces sphingolipid ceramide N-deacylase, *Shewanella* alga NS-589, has been deposited on Jun. 26, 1996 under accession number FERM P-15700. Both of the strains have been deposited at the National Institute of Bioscience and Human-Technology, Agency of Industrial Science and Technology, Ministry of International Trade and Industry, 1–3, Higashi 1-chome, Tsukuba-shi, Ibaraki-ken, Japan.

These enzymes can be used in enzyme solutions or being immobilized onto water-insoluble carries.

Water or an aqueous solution is used for an aqueous phases in the present invention. Specifically, a buffer to which an enzyme and a substrate and the like for a variety of reactions are added is preferable.

A separation phase is a phase of an organic solvent immiscible with water. The organic solvent is selected from the group consisting of a hydrocarbon, an alcohol, an ester, an ether and a ketone such that, between the organic solvent phase and the aqueous phase, the partition ratio of a fatty acid (which is a degradation product of a sphingolipid) in the organic solvent phase is higher than that in the aqueous phase, and such that the partition ratio of the sphingolipid as a substrate in the organic phase is lower than that in the aqueous phase.

The organic solvents include, but are not limited to, for example, hydrocarbons including an aliphatic hydrocarbon such as hexane, heptane, octane, isooctane, nonane, decane, dodecane, pentadecane, heptadecane, octadecane, 2-methylpentane, 2,2-dimethylbutane, 2,2,3-trimethylheptane, 2,2,4-trimethylheptane, hexene, octene, decene, dodecene, pentadecene and heptadecene, an aliphatic cyclic hydrocarbon such as cyclohexane, methylcyclohexane, cyclodecane, cyclohexene and cyclodecene, a halogen-containing hydrocarbon such as dichloroethane, tetrachloroethane, trichloroethylene, carbon tetrachloride, octyl chloride, desyl chloride, chlorobenzene and dichlorobenzene, as well as an aromatic hydrocarbon such as benzene, toluene, xylene, mesitylene, ethylbenzene, butylbenzene, cumene and cymene.

Alcohols include octanol, decanol, dodecanol, octen-ol, decen-ol and cyclodecanol.

Esters include ethyl hexanoate, ethyl octanoate, ethyl decanoate, ethyl dodecanoate, isopropyl mystirate, butyl stearate, butyl citrate and ethyl citrate.

Ethers include phenyl ether, vinyl ethyl ether, ethylene glycol diethyl ether, diisopropyl ether and octyl ether.

Ketones include octanone, decanone and dodecanone.

Among the organic solvents as listed above, hydrocarbons of six carbons or more (including aliphatic, cyclic, aromatic and halogen-containing hydrocarbons), alcohols of eight carbons or more, esters composed of a carboxylic acid of six carbons or more and an alcohol of two carbons or more, as well as ethers selected from the group consisting of phenyl ether, ethylene glycol diethyl ether, diisopropyl ether and vinyl ethyl ether can be preferably used in the process of the present invention in particular.

Furthermore, the number of the organic solvent to be used in the present invention is not limited to one. Two or more organic solvents can be mixed and used.

The two-phase systems in the present invention include those in which the aqueous phase and the organic solvent phase are in a state in which an aqueous phase is dispersed in an organic solvent phase or in a state in which an organic solvent phase is dispersed in an aqueous phase, for example, by stirring, or in a state in which an aqueous phase and an organic solvent phase are separated into two phases contacting each other, for example, by settling without dispersion.

Alternatively, the organic solvent phase and/or the aqueous phase may be occasionally exchanged while continuing the enzymatic reaction, which makes the continuous production of a lysosphingolipid possible. The amount of the organic solvent to be added may be, without limitation, preferably 50% or more, usually 5–10 times of the volume of the aqueous phase.

Various salts and surfactants can be added to an aqueous phase. For example, at least one selected from the group consisting of a surfactant having a steroid backbone such as sodium taurodeoxycholate and sodium cholate, a polyoxyethylene alkyl phenyl ether such as a Triton-type surfactant and Nonidet P-40™, a polyoxyethylene sorbitan alkyl ether such as a Tween-type surfactant, and a non-ionic surfactant such as polyoxyethylene alkyl ether can be added. Preferably, the amount of a surfactant is, without limitation, usually 0.1–2% by weight based on the total volume of the reaction system.

There is no limitation regarding the reaction conditions. A lysosphingolipid can be produced more efficiently by reacting under optimal conditions for the respective enzyme used, including pH and temperature.

For example, when sphingolipid ceramide N-deacylase produced by a bacterium of genus *Pseudomonas* is used in a reaction, it is preferred to conduct the reaction at pH 6–10 by adding a surfactant having a steroid backbone such as sodium taurodeoxycholate or sodium cholate. In addition, a sphingolipid can be hydrolyzed more efficiently by using a polyoxyethylene alkyl phenyl ether such as Triton X-100™ or Nonidet P-40™ in combination.

There is no limitation regarding the reaction time. The reaction may be conducted for a period of time required for obtaining a desired amount of a lysosphingolipid using an enzyme from a substrate to be used such as a naturally occurring or synthetic sphingolipid including a glycosphingolipid, a sphingophospholipid and a ceramide.

A lysosphingolipid produced by the present invention can be purified according to a conventional method.

The organic solvent may be removed from the reaction mixture by separating into two phases after settlement or by using a selective membrane or a column. Alternatively, the solvent may be removed by concentration under reduced pressure or by distillation.

The thus-obtained reaction mixture containing a lysoform in an aqueous phase contains less contaminant. Therefore, the lysosphingolipid can be readily purified by using a conventional extraction method such as reversed phase chromatography, normal phase chromatography with silica gel or ion exchange chromatography.

Furthermore, a fatty acid derived from a sphingolipid can be obtained by evaporating the organic solvent from the organic phase separated in the above-mentioned step for removal.

The structure of the purified lysosphingolipid can be confirmed by analysis with thin-layer chromatography, liquid chromatography, mass spectrometry, nuclear magnetic resonance spectrometry or the like.

As described above, a sphingolipid can be converted into a lysosphingolipid of interest according to the process of the present invention.

Additionally, a lysosphingolipid derivative can be produced by treating a lysosphingolipid obtained by the present invention. For example, a lysosphingolipid derivative can be produced as follows.

Re-acylation can be conducted according to a chemical or enzymatic conventional method for acid amidation of an amino group.

In a chemical re-acylation, a reaction may be conducted by using an apliphatic carboxylic acid or a reactive derivative thereof with or without a label. Examples of aliphatic carboxylic acids which can be used in the present invention include a saturated fatty acid, an unsaturated fatty acid, as well as all of the carboxylic acids having an aliphatic property such as an acid in which the hydrocarbon chain of the fatty acid is replaced by a halogen or a functional group such as a substituted or unsubstituted amino group, an oxo group, or a hydroxyl group, or an acid having hydrogen, sulfur or an amino group in the hydrocarbon chain.

An enzymatic re-acylation may be achieved by using known lipase. In a particularly useful method, the re-acylation can be readily conducted by utilizing a reverse reaction of an enzyme that specifically hydrolyzes an acid amide bond between a sphingoid and a fatty acid in a sphingolipid, for example, the above-mentioned sphingolipid ceramide N-deacylase (WO 98/03529).

Labeling of the amino group of the sphingoid in the resulting lysosphingolipid may be achieved by introducing a substance that forms a chromophore, a fluorescent substance, biotin, a radioisotope or the like into a portion to be labeled.

The following Examples illustrate the present invention in more detail, but are not to be construed to limit the scope thereof.

EXAMPLE 1

Production of Lysosphingolipid by Addition of Various Organic Solvents

A 100 µl each aliquot of various organic solvents was added to 10 µl of 50 mM acetate buffer (pH 6.0) containing 2 mU of sphingolipid ceramide N-deacylase from a bacterium of genus Pseudomonas, Pseudomonas sp. TK-4 (FERM BP-5069) [SCDase; Journal of Biological Chemistry, 270:24370–24374 (1995); JP-A 8-84587], 0.8% sodium taurodeoxycholate (nacalai tesque) and 10 nmol GM1 (Matreya). The mixture was incubated at 37° C. for 16 hours. A mixture without an organic solvent was similarly incubated as a control.

The resulting reaction mixture was developed using thin-layer chromatography. The TCL plate was visualized using orcinol-sulfuric acid. Then, the yield of the lyso-form of GM1 was quantified using an imaging densitometer (Bio-Rad). The results are shown in Table 1.

Among the organic solvents listed in Table 1 below, cyclodecane is from Aldrich and all of the others are from nacalai tesque.

TABLE 1

| Solvent | Yield of lyso-form (%) |
| --- | --- |
| Control | 68 |
| 1-Butanol | 44 |
| 1-Pentanol | 51 |
| 1-Hexanol | 53 |
| 1-Heptanol | 62 |
| 1-Octanol | 70 |
| 2-Octanol | 90 |
| 1-Decanol | 83 |
| 1-Dodecanol | 100 |
| Hexane | 76 |
| Octane | 89 |
| Decane | 95 |

TABLE 1-continued

| Solvent | Yield of lyso-form (%) |
| --- | --- |
| Pentadecane | 97 |
| Heptadecane | 97 |
| Octadecane | 97 |
| 1-Hexene | 80 |
| 1-Octene | 91 |
| 1-Decene | 94 |
| 1-Dodecene | 93 |
| Cyclohexane | 87 |
| Methylcyclohexane | 93 |
| Cyclodecane | 89 |
| Benzene | 70 |
| Toluene | 84 |
| Xylene | 95 |
| Mesitylene | 97 |
| n-Ethylbenzene | 97 |
| n-Butylbenzene | 99 |
| p-Cymene | 98 |
| Cumene | 96 |
| n-Octyl chloride | 99 |
| n-Desyl chloride | 100 |
| Chloroform | 62 |
| Carbon tetrachloride | 73 |
| Ethyl acetate | 58 |
| Butyl acetate | 68 |
| Hexyl acetate | 60 |
| Phenyl acetate | 55 |
| Benzyl acetate | 67 |
| Methyl hexanoate | 47 |
| Methyl octanoate | 61 |
| Methyl decanoate | 62 |
| Methyl dodecanoate | 68 |
| Ethyl propionate | 58 |
| Ethyl butyrate | 54 |
| Ethyl hexanoate | 73 |
| Ethyl octanoate | 73 |
| Ethyl decanoate | 75 |
| Ethyl dodecanoate | 74 |
| Isopropyl myristate | 91 |
| n-Butyl stearate | 84 |
| Phenyl ether | 97 |
| Ethyl ether | 41 |
| Propyl ether | 54 |
| Butyl ether | 64 |
| Vinyl ethyl ether | 73 |
| Vinyl butyl ether | 61 |
| Ethylene glycol diethyl ether | 71 |
| Diisopropyl ether | 91 |

EXAMPLE 2

Examination of Surfactant

A 100 µl aliquot of n-decane (nacalai tesque) was added to 10 µl of 50 mM acetate buffer (pH 6.0) containing 2 mU of SCDase from a bacterium of genus Pseudomonas [Journal of Biological Chemistry, 270:24370–24374 (1995); JP-A 8-84587], one of various surfactants and 10 nmol GM1 (Matreya). The mixture was incubated at 37° C. for 16 hours.

The resulting reaction mixture was developed using thin-layer chromatography. The TLC plate was visualized using orcinol-sulfuric acid. Then, the yield of the lyso-form of GM1 was quantified using an imaging densitometer (Bio-Rad) as described in Example 1. The results are shown in Table 2.

The final concentration of the surfactant was 0.8% by weight based on the volume of the reaction system. Among the surfactants listed in Table 2 below, Triton X-100™ is from Pierce and all of the others are from nacalai tesque.

TABLE 2

| Surfactant | Yield of lyso-form (%) |
|---|---|
| No addition | 25 |
| Sodium taurodeoxycholate | 99 |
| Sodium cholate | 92 |
| Triton X-100 ™ | 64 |
| Tween 20 ™ | 42 |
| Nonidet P-40 ™ | 60 |
| Brij-58 ™ | 66 |
| Lubrol PX ™ | 72 |

EXAMPLE 3

Examination of Concentration of Sodium Taurodeoxycholate

A 100 µl aliquot of n-heptadecane (nacalai tesque) was added to 10 µl of 50 mM acetate buffer (pH 6.0) containing 2 mU of SCDase from a bacterium of genus *Pseudomonas* [Journal of Biological Chemistry, 270:24370–24374 (1995); JP-A 8-84587], varying concentration of sodium taurodeoxycholate (nacalai tesque) and 10 nmol GM1 (Matreya). The mixture was incubated at 37° C. for 16 hours.

The resulting reaction mixture was developed using thin-layer chromatography. The TLC plate was visualized using orcinol-sulfuric acid. Then, the yield of the lyso-form of GM1 was quantified using an imaging densitometer (Bio-Rad) as described in Example 1. The results are shown in Table 3. The concentration of the surfactant in Table 3 is the final concentration expressed as % by weight based on the volume of the reaction system.

TABLE 3

| Concentration | Yield of lyso-form (%) |
|---|---|
| 0 | 25 |
| 0.05 | 55 |
| 0.01 | 65 |
| 0.2 | 80 |
| 0.4 | 88 |
| 0.8 | 92 |
| 1.0 | 92 |

EXAMPLE 4

Examination of Optimal pH

A 100 µl aliquot of n-decane (nacalai tesque) was added to 10 µl of one of various buffers at 50 mM containing 2 mU of SCDase from a bacterium of genus *Pseudomonas* [Journal of Biological Chemistry, 270:24370–24374 (1995); JP-A 8-84587], 0.8% sodium taurodeoxycholate (nacalai tesque) and 10 nmol GM1 (Matreya). The mixture was incubated at 37° C. for 16 hours. The following buffers were used: an acetate buffer for pH 3–6; a phosphate buffer for pH 6–8; a Tris-HCl buffer for pH 8–9; and a glycine-NaOH buffer for pH 9–10.

The resulting reaction mixture was developed using thin-layer chromatography. The TLC plate was visualized using orcinol-sulfuric acid. Then, the degradation rate of GM1, i.e., the yield of the lyso-form was quantified using an imaging densitometer (Bio-Rad) as described in Example 1. The results are shown in FIG. 1.

FIG. 1 depicts the optimal pH for the yield of a lyso-form in the presence of an organic solvent. In the figure, the vertical axis and the horizontal axis represent degradation rate (%) and pH, respectively. The open circles, the closed circles, the open triangles and the closed squares represent results obtained by using an acetate buffer, a phosphate buffer, a Tris-HCl buffer and a glycine-NaOH buffer, respectively.

EXAMPLE 5

Substrate Specificity in the Presence of Organic Solvent

A 100 µl aliquot of n-heptadecane (nacalai tesque) was added to 10 µl of 50 mM acetate buffers (pH 6.0) containing 2 mU of SCDase from a bacterium of genus *Pseudomonas* [Journal of Biological Chemistry, 270:24370–24374 (1995); JP-A 8-84587], 0.8% sodium taurodeoxycholate (nacalai tesque) and 10 nmol each of various substrates. The mixture was incubated at 37° C. for 16 hours. A reaction mixture without n-heptadecane was prepared as a control. The following substrates were used: ceramide (Cer); galactosylceramide (GalCer); sulfatide; GM1; asialo GM1; GD1a; sphingomyelin (all from Matreya).

Among the resulting reaction mixtures, the yield of the lyso-form from ceramide was quantified by developing on thin-layer chromatography and visualizing the generated sphingosine using a ninhydrin reagent. The yield of sphingomyelin was quantified by visualizing the generated lysosphingomyelin using Coomassie Brilliant Blue. The reaction mixtures containing the other substrates were developed using thin-layer chromatography. The TLC plate was visualized using orcinol-sulfuric acid. Then, the yields of the lyso-forms from the respective substrates were quantified using an imaging densitometer (Bio-Rad) as described in Example 1. The results are shown in FIG. 2.

Figure 2:
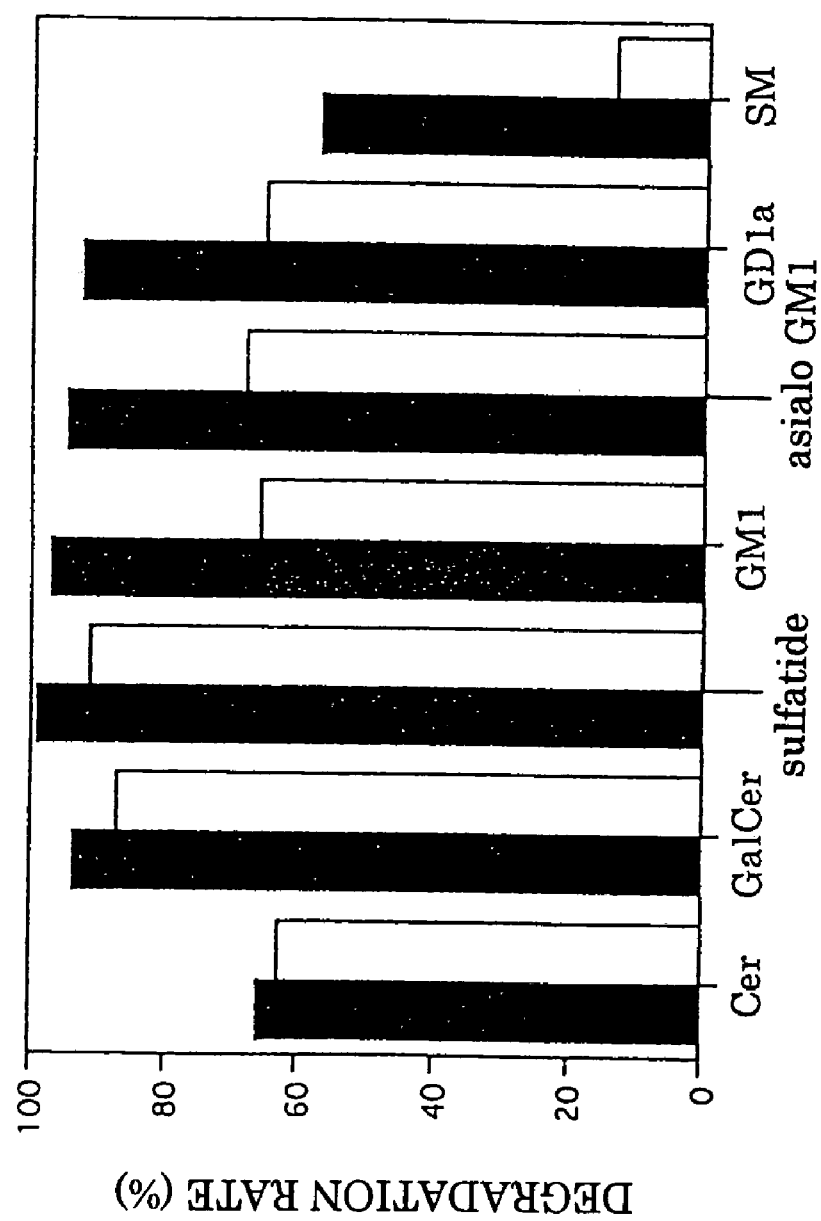
FIG. 2 depicts the substrate specificity that affects the yield of a lyso-form in the presence or absence of an organic solvent.

FIG. 2 depicts the substrate specificity that affects the yield of a lyso-form in the presence or absence of an organic solvent. In the figure, the vertical axis and the horizontal axis represent yield (%) and the various substrates. The closed bars represent the degradation rate in the presence of n-heptadecane, and the open bars represent the degradation rate in the absence of n-heptadecane.

EXAMPLE 6

Time Course of Yield of Lyso-Form in the Presence or Absence of Sodium Taurodeoxycholate, Triton X-100™ and Organic Solvent After a reaction at 37° C. under the reaction conditions (A)–(D) as described below for a period of 0, 0.5, 1, 2, 6 or 16 hour, the yield was quantified. The resulting reaction mixture was developed using thin-layer chromatography. The TLC plate was visualized using orcinol-sulfuric acid. Then, the degradation rate of GM1, i.e., the yield of the lyso-form was quantified using an imaging densitometer (Bio-Rad) as described in Example 1. The results are shown in FIG. 3.

Figure 3:
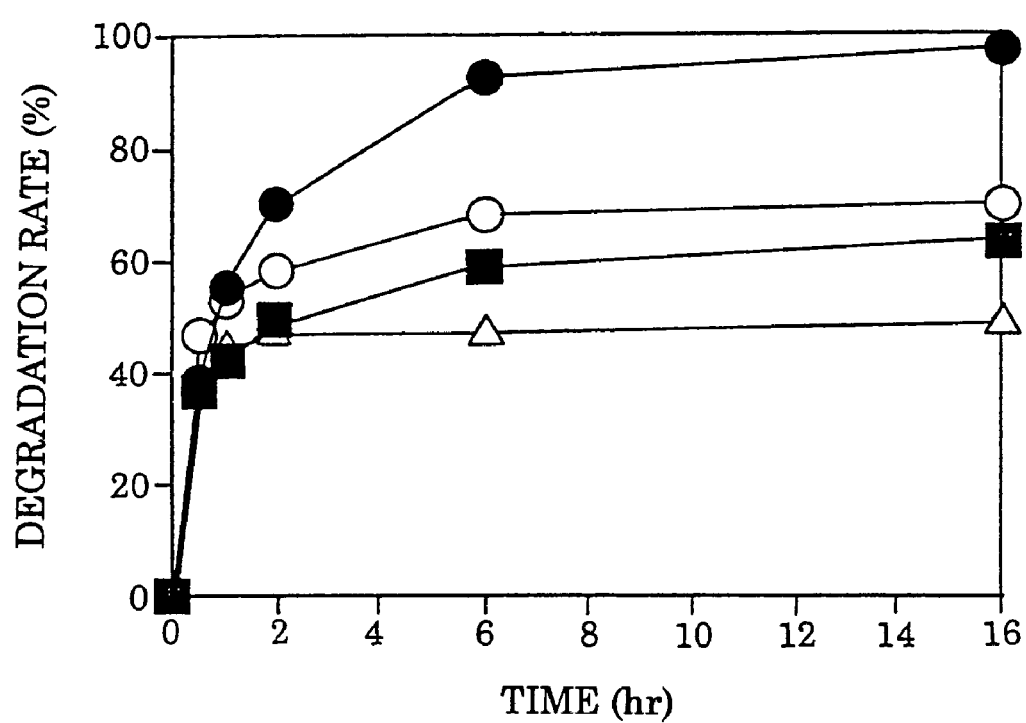
FIG. 3 depicts the time course of the yield of a lyso-form in the presence or absence of a surfactant and an organic solvent.

FIG. 3 depicts the time course of the degradation rate of GM1 in the presence or absence of a surfactant and an organic solvent. In the figure, the vertical axis and the horizontal axis represent degradation rate (%) and time (hr), respectively. The symbols represent the results obtained in the presence of the following: sodium taurodeoxycholate and n-decane (closed circle); sodium taurodeoxycholate (open circle); Triton X-100™ and n-decane (closed square); or Triton X-100™ (open triangle).

Reaction conditions (A): A 100 µl aliquot of n-decane (nacalai tesque) was added to 10 µl of 50 mM acetate buffers (pH 6.0) containing 2 mU of SCDase from a bacterium of genus *Pseudomonas* [Journal of Biological Chemistry, 270:

24370–24374 (1995); JP-A 8-84587], 0.8% sodium taurodeoxycholate (nacalai tesque) and 10 nmol GM1 (Matreya) and incubated.

Reaction conditions (B): A 10 µl aliquot of 50 mM acetate buffers (pH 6.0) containing 2 mU of SCDase from a bacterium of genus *Pseudomonas*, 0.8% sodium taurodeoxycholate and 100 nmol GM1 was incubated.

Reaction conditions (C): A 100 µl aliquot of n-decane was added to 10 µl of 50 mM acetate buffers (pH 6.0) containing 2 mU of SCDase from a bacterium of genus *Pseudomonas*, 0.8% Triton X-100™ (Pierce) and 10 nmol GM1 and incubated.

Reaction conditions (D): A 10 µl aliquot of 50 mM acetate buffers (pH 6.0) containing 2 mU of SCDase from a bacterium of genus *Pseudomonas*, 0.8% Triton X-100™ and 10 nmol GM1 was incubated.

EXAMPLE 7

Examination of Yield of Lyso-Form in the Presence of Sodium Taurodeoxycholate, Triton X-100™ and Organic Solvent A 100 µl aliquot of n-heptadecane (nacalai tesque) was added to 10 µl of 50 mM acetate buffer (pH 6.0) containing 0.5 mU of SCDase from a bacterium of genus *Pseudomonas* [Journal of Biological Chemistry, 270:24370–24374 (1995); JP-A 8-84587], 0.8% sodium taurodeoxycholate (nacalai tesque), 0, 0.1, 0.4 or 0.8% Triton X-100™ (Pierce) and 10 nmol GM1 (Matreya) and incubated at 37° C. for 16 hours.

The resulting reaction mixture was developed using thin-layer chromatography. The TLC plate was visualized using orcinol-sulfuric acid. Then, the degradation rate of GM1, i.e., the yield of the lyso-form was quantified using an imaging densitometer (Bio-Rad) as described in Example 1. The results are shown in FIG. 4.

Figure 4:
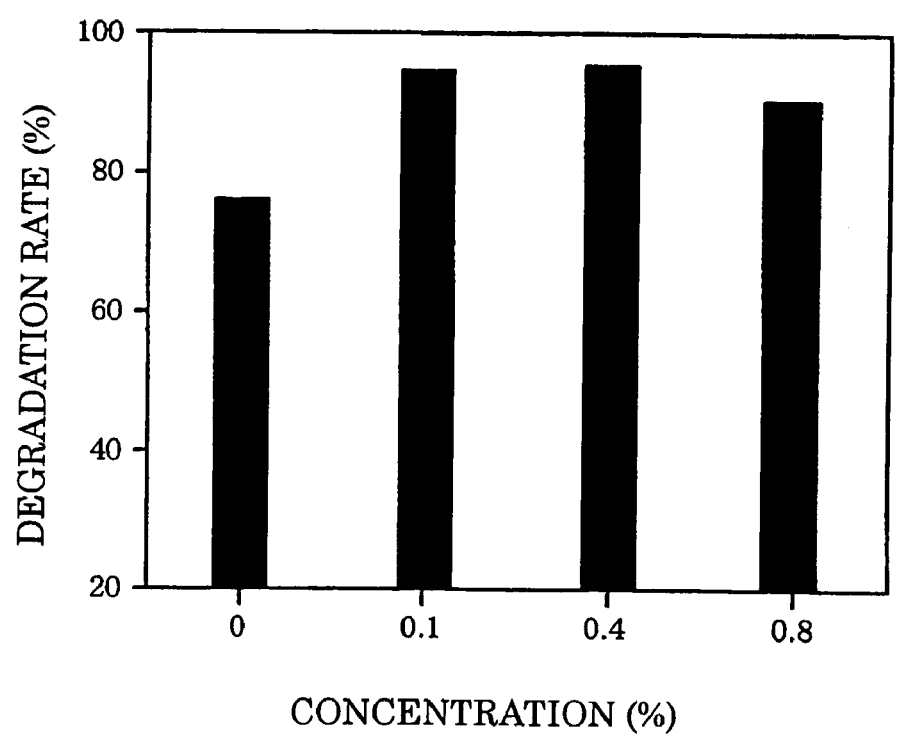
FIG. 4 depicts the yield of a lyso-form using varying amount of an enzyme in the presence of an organic solvent.

FIG. 4 depicts the degradation rate of GM1 using varying amount of an enzyme in the presence of sodium taurodeoxycholate, varying concentration of Triton X-100™ and an organic solvent. In the figure, the vertical axis and the horizontal axis represent degradation rate (%) and concentration of Triton X-100™ (%), respectively.

EXAMPLE 8

Examination of Amount of Organic Solvent

Varying amount of n-decane (nacalai tesque) or n-heptadecane (nacalai tesque) was added to 10 µl of 50 mm acetate buffer (pH 6.0) containing 2 mU of SCDase from a bacterium of genus *Pseudomonas* [Journal of Biological Chemistry, 270:24370–24374 (1995); JP-A 8-84587], 0.8% sodium taurodeoxycholate (nacalai tesque), 0.1% Triton X-100™ (Pierce) and 10 nmol GM1 (Matreya). The mixture was incubated at 37° C. for 16 hours.

The resulting reaction mixture was developed using thin-layer chromatography. The TLC plate was visualized using orcinol-sulfuric acid. Then, the degradation rate of GM1, i.e., the yield of the lyso-form was quantified using an imaging densitometer (Bio-Rad) as described in Example 1. The results are shown in FIG. 5.

Figure 5:
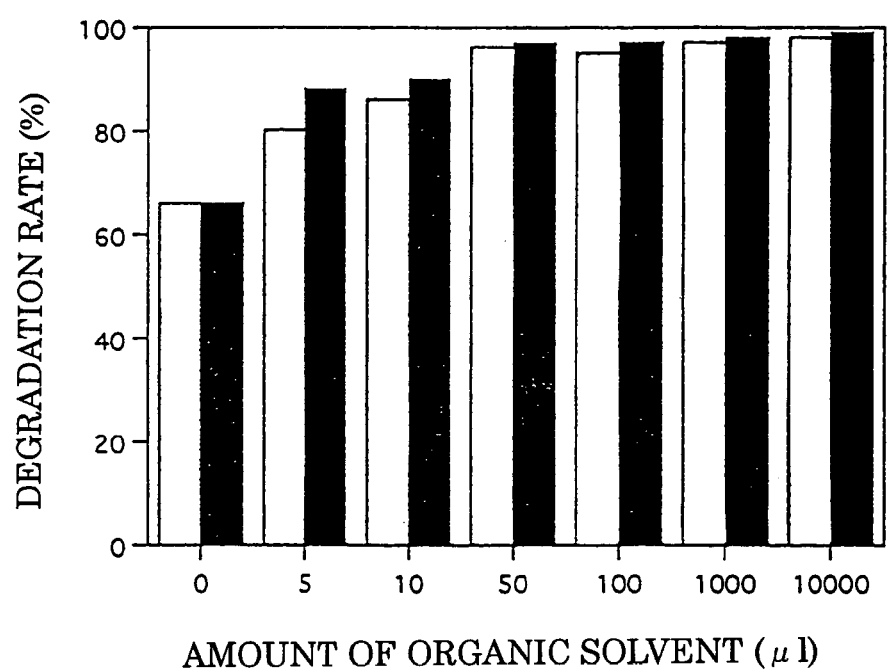
FIG. 5 depicts the relationship between the amount of added organic solvent and the yield of a lyso-form.

FIG. 5 depicts the relationship between the amount of the organic solvent and the yield of the lyso-form. In the figure, the vertical axis and the horizontal axis represent degradation rate (%) and amount of organic solvent (µl). The open bars represent the results for n-decane, and the closed bars represent the results for n-heptadecane.

EXAMPLE 9

Examination of Various Surfactants Using Low Concentration of Enzyme

A 100 µl aliquot of n-heptadecane (nacalai tesque) was added to 10 µl of 50 mM acetate buffer (pH 6.0) containing 0.5 mU of SCDase from a bacterium of genus *Pseudomonas* [Journal of Biological Chemistry, 270:24370–24374 (1995); JP-A 8-84587], one of various surfactants and 10 nmol GM1 (Matreya). The mixture was incubated at 37° C. for 16 hours.

The resulting reaction mixture was developed using thin-layer chromatography. The TLC plate was visualized using orcinol-sulfuric acid. Then, the yield of the lyso-form of GM1 was quantified using an imaging densitometer (Bio-Rad) as described in Example 1. The results are shown in Table 4.

The final concentration of the surfactant was 0.1% by weight based on the volume of the reaction system. Among the surfactants listed in Table 4 below, Triton X-100™ is from Pierce and all of the others are from nacalai tesque.

TABLE 4

| Surfactant | Yield of lyso-form (%) |
|---|---|
| Triton X-100 ™ | 39 |
| Tween 20 ™ | 51 |
| Tween 80 ™ | 69 |
| Nonidet P-40 ™ | 64 |
| Brij-58 ™ | 65 |
| Lubrol PX ™ | 67 |

EXAMPLE 10

Examination of Yield of Lyso-Form Using Mixture Containing Sodium Taurodeoxycholate and Various Surfactants A 100 µl aliquot of n-heptadecane (nacalai tesque) was added to 10 µl of 50 mM acetate buffer (pH 6.0) containing 0.5 mU of SCDase from a bacterium of genus *Pseudomonas* [Journal of Biological Chemistry, 270:24370–24374 (1995); JP-A 8-84587], 0.8% sodium taurodeoxycholate, one of various surfactants and 10 nmol GM1 (Matreya). The mixture was incubated at 37° C. for 16 hours. A mixture containing sodium taurodeoxycholate alone was reacted as a control.

The resulting reaction mixture was developed using thin-layer chromatography. The TLC plate was visualized using orcinol-sulfuric acid. Then, the yield of the lyso-form of GM1 was quantified using an imaging densitometer (Bio-Rad) as described in Example 1. The results are shown in Table 5.

The final concentration of the surfactant in the mixture was 0.1% by weight based on the volume of the reaction system. Among the surfactants listed in Table 5 below, Triton X-100™ is from Pierce and all of the others are from nacalai tesque.

TABLE 5

| Surfactant in mixture | Yield of lyso-form (%) |
|---|---|
| Control | 53 |
| Triton X-100 ™ | 70 |
| Nonidet P-40 ™ | 68 |
| Tween 20 ™ | 48 |
| Tween 80 ™ | 50 |
| Brij-58 ™ | 53 |
| Lubrol PX ™ | 57 |

EXAMPLE 11

Production of Lysoganglioside GM3

10 mg of ganglioside GM3 (Matreya) was dissolved in 10 ml of 50 mM acetate buffer (pH 6.0) containing 0.8% sodium taurodeoxycholate. The mixture was placed into a 200 ml pear-shaped flask, and then 2 U of SCDase was added thereto. A 100 ml aliquot of n-decane was overlaid thereon, and the mixture was allowed to stand at 37° C. for 16 hours. 1 U of SCDase was added to the aqueous phase, and the mixture was incubated at 37° C. for additional 16 hours. At that time, the degradation rate of ganglioside GM3 was 95%.

After the reaction was completed, the aqueous phase was recovered, divided into two equal parts and subjected to purification using reversed phase chromatography. The aqueous phase was added to POROS R2H column (φ 4.6×100 mm, PerSeptive), and then gradient elution from acetonitrile:water=10:90 to acetonitrile:methanol=10:90 was conducted. The eluted fractions containing lysoganglioside GM3 were collected and concentrated to dryness. As a result, 5.6 mg of a lyso-form with a purity of 95% or more was obtained as demonstrated by thin-layer chromatography visualized using orcinol-sulfuric acid and a bichromic acid-sulfuric acid mixture.

As described above, a large amount of lysosphingolipid can be industrially prepared efficiently, readily and with high purity by the process for production of the present invention.

The invention claimed is:

1. A process for producing a lysosphingolipid by using a sphingolipid ceramide N-deacylase, the method comprising:
    a. preparing an aqueous solution containing sphingolipid and a sphingolipid ceramide N-deacylase that is soluble in the aqueous solution;
    b. adding at least one organic solvent which is immiscible with water to the aqueous solution prepared in step (a) and forming a two-phase system reaction mixture, wherein said organic solvent is selected from the group consisting of:
        (i) a hydrocarbon which is selected from the group consisting of, octane, decane, pentadecane, heptadecane, octadecane, 1-octene, 1-decene, 1-dodecene, methylcyclohexane, cyclodecane, toluene, xylene, mesitylene, n-ethylbenzene, n-butylbenzene, p-cymene, cumene, n-octyl chloride, and n-desyl chloride;
        (ii) an alcohol which is selected from the group consisting of 2-octanol, 1-decanol, and 1-dodecanol;
        (iii) an ester which is selected from the group consisting of isopropyl myristate, and n-butyl stearate; and
        (iv) an ether which is selected from the group consisting of phenyl ether, and diisopropyl ether; and;
    c. allowing the two-phase system reaction mixture formed in step (b) to stand by settling without dispersion for a period of time sufficient to produce a lysosphingolipid.

2. The process according to claim 1, wherein the aqueous solution contains at least one surfactant.

3. The process according to claim 2, wherein the surfactant is selected from the group consisting of surfactants having a steroid backbone, polyoxyethylene alkyl phenyl ethers, polyoxyethylene sorbitan alkyl ethers, and polyoxyethylene alkyl ethers.

* * * * *

UNITED STATES PATENT AND TRADEMARK OFFICE
CERTIFICATE OF CORRECTION

| | | |
|---|---|---|
| PATENT NO. | : 7,045,322 B1 | |
| APPLICATION NO. | : 09/647135 | |
| DATED | : May 16, 2006 | |
| INVENTOR(S) | : Kurita et al. | |

It is certified that error appears in the above-identified patent and that said Letters Patent is hereby corrected as shown below:

On the Title page, Item (73) Assignee, delete "TAKARA SHUZO CO. LTD", and insert --TAKARA BIO INC.--.

Signed and Sealed this
Seventeenth Day of July, 2012

David J. Kappos
*Director of the United States Patent and Trademark Office*